United States Patent [19]

Vegezzi

[11] 4,122,179

[45] Oct. 24, 1978

[54] ACID ADDITION SALTS OF VINCAMINE AND APOVINCAMINE

[75] Inventor: Davide Vegezzi, Massagno (Lugano), Switzerland

[73] Assignee: Enrico Corvi Mora, Piacenza, Italy

[21] Appl. No.: 801,209

[22] Filed: May 27, 1977

[30] Foreign Application Priority Data

Jun. 3, 1976 [CH] Switzerland ............... 7039/76
Jun. 3, 1976 [CH] Switzerland ............... 7040/76

[51] Int. Cl.² ............... C07D 519/04; A61K 31/725; C08B 37/06
[52] U.S. Cl. ............... 424/180; 260/293.53; 260/293.55; 424/253; 424/256; 424/266; 536/2; 536/3; 536/117; 544/268
[58] Field of Search ............ 260/293.53, 293.55, 260/251 A, 253; 424/267, 256, 180, 253, 266; 536/2, 3, 117

[56] References Cited

U.S. PATENT DOCUMENTS 3,925,393  12/1975  Heurtaux et al. ............ 260/293.53
3,982,002   9/1976  Montoro et al. ............ 424/267

FOREIGN PATENT DOCUMENTS 585,226  2/1977  Switzerland ............ 260/293.55

Primary Examiner—Henry R. Jiles
Assistant Examiner—Richard A. Schwartz
Attorney, Agent, or Firm—Stevens, Davis, Miller & Mosher

[57] ABSTRACT

The invention relates to vasodilating derivatives of vincamine and apovincamine having the general formula

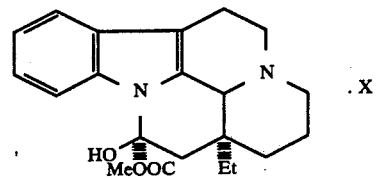

wherein X represents either the radical of an organic acid or a compound forming an adduct with vincamine and apovincamine. These derivatives, apart from the therapeutical action possessed by the vincamine and apovincamine respectively, are also endowed with an extended effect. The invention relates too to the method for the preparation of the above derivatives and to the pharmaceutical compositions containing these derivatives as the active ingredient.

37 Claims, No Drawings

ACID ADDITION SALTS OF VINCAMINE AND APOVINCAMINE

The present invention relates to novel derivatives of vincamine and apovincamine having interesting therapeutical properties at the cardiovascular level and, generally, for the circulatory system.

The vincamine having the formula:

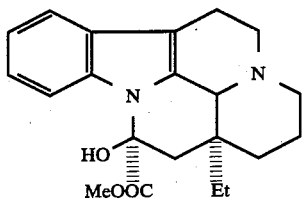

and the apovincamine, having the formula:

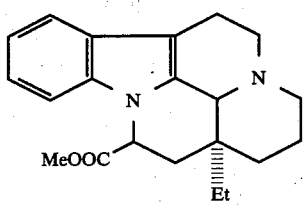

are substances already known and used in the therapy of the cerebral arteriosclerosis, owing to their effective action at the cerebral level and, furthermore, due to their capacity of activating the metabolism of the nervous cells.

However their therapeutical action, through the several administration routes, is characterized by a short duration, as a consequence of the ready elimination thereof, whereby repeated administrations, within the 24 hour period, are necessary.

It has been found, which is the subject of the present invention, that some derivatives of the vincamine and the apovincamine are endowed with the property of possessing the same therapeutical activity, combined with an effect which is prolonged in the time, namely of the so-called long-acting type, said derivatives having the following general formula:

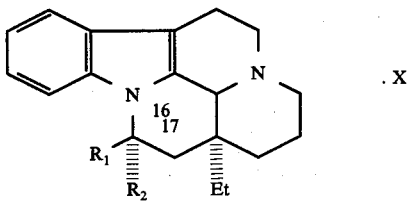

wherein, if $R_1$ represents OH, $R_2$ represents MeOOC, or if $R_1$ represents MeOOC, a double bond is present in the position $\Delta^{16,17}$, and X represents a group selected in the class comprising glucose1-phosphate, (neutral and acid salts), glucose-1-phosphate disodium, glucose-6-phosphate (neutral and acid salt and disodium adduct), 2,6-, 2,5-, 2,4-, and 3,5-dihydroxy-benzoic acids, p-toluenesulphonic acid, clofibric (or 2-(p-chlorophenoxy)-2-methylpropionic) acid, pivalic acid, 4-acetamidobutyric acid, 2-furoic acid, I(+)-0,0-dibenzoyltartaric acid, methylsulfuric acid, enanthic acid, p-chlorophenoxyacetic acid, theophylline-7-acetic acid, caproic acid, capric acid, alginic acid, tannic acid, (D,L)-mandelic acid, indolyl-3-acetic acid, salycilic acid, hydroquinone, dihydroxyphenylalanine and pectine.

In turn the general process for preparing the compounds of the present invention comprises reacting vincamine or apovincamine, according to the desired derivative, in form of a solution or of a suspension, with the compound originating the group X, preferably in form of a solution, the reaction being carried out in hot condition, under controlled temperature and under stirring until the end of the reaction, and then separating the reaction product.

The particular features and the details of the preparation of the novel compounds of the present invention will clearly appear from the following examples, having illustrative but not limitative purpose. The examples are particularly referred to the glucose-1-phosphate, but the operating conditions are essentially identical for the derivatives of the glucose-6-phosphate.

EXAMPLE 1

1.a

Vincamine glucose-1-phosphate disodium

It is an equimolecular adduct ($C_{21}H_{26}N_2O_3 \cdot C_6H_{11}Na_2O_9P$) having the formula:

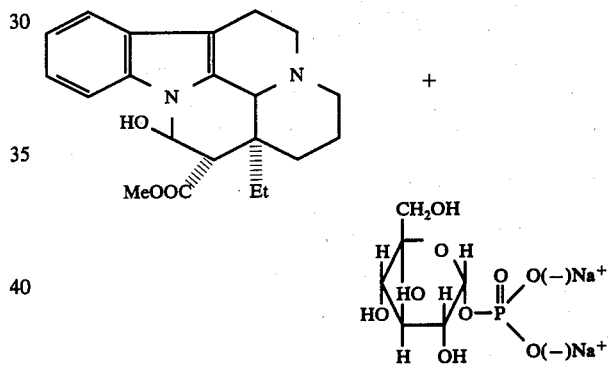

3.54 g ($10^{-2}$ moles) of vincamine are dissolved in a mixture of 180 mls of ethyl alcohol and 25 mls of $CHCl_3$, at 70° C. in a water bath and under stirring.

A solution comprising 3.76 g ($10^{-2}$ moles) of the disodium salt of glucose-1-phosphate tetrahydrate ($C_6H_{11}Na_2O_9P \cdot 4H_2O$) in 20 mls of water is added dropwise.

The mixture is maintained in the hot condition and under stirring for 30 minutes and then the reaction mixture is mass concentrated to a final volume of about 50 mls.

60 mls of alcohol are further added and the solvent is distilled until a residue is obtained.

This step is repeated twice, a final volume of about 10 mls being attained at the end.

The precipitation is completed by keeping the mixture on standing in an ice bath.

After filtration and drying of the product in an aerated furnace at 60° C., 7.2 g are obtained of a white crystalline substance, not soluble in water and alcohol, having a total melting point of about 240° C.

The content of vincamine in the adduct is 55%. The above procedure is repeated, by only varying the ratio of the two reactants, which are respectively 2.5 g of vincamine and 7.5 g of the disodium salt of glucose-1-phosphate tetrahydrate.

9.8 g are obtained of a product identical to the preceding one, with a vincamine content of 26%.

1.b

Apovincamine glucose-1-phosphate disodium

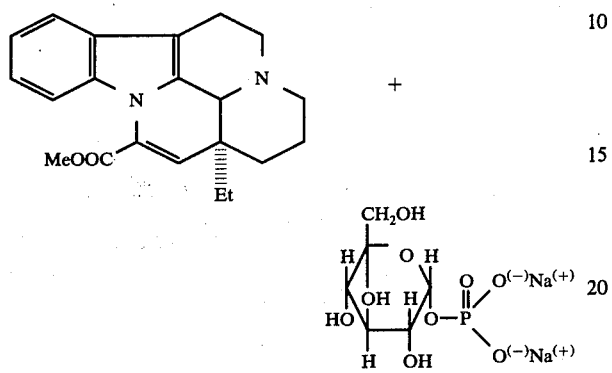

The procedure of Example 1 is repeated, except that the adduct is prepared from 3.36 g ($10^{-2}$ moles) of apovincamine and 3.76 g of the disodium salt of glucose-1-phosphate tetrahydrate.

7 g are obtained of a white crystalline substance, not soluble in water and alcohol, and having a point of complete melting of about 160°–165° C.

The content of apovincamine in the adduct is 53.1%. The above procedure is repeated, by only varying the ratio of the two reactants, which are respectively 2.5 g of apovincamine and 7.5g of the disodium salt of glucose-1-phosphate tetrahydrate.

9.8 g are obtained of a product identical to the preceding one, with an apovincamine content of 26%.

EXAMPLE 2

2.a

Vincamine 2,4-dihydroxy-benzoate (vincamine beta-resorcylate)

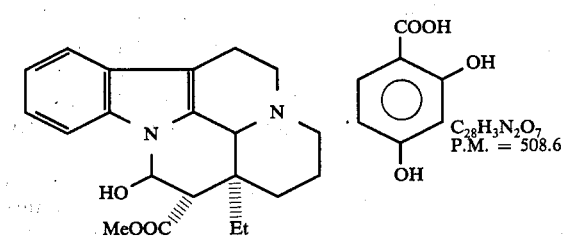

A suspension of 7.08 g ($2.10^{-2}$ moles) of vincamine in 100 mls of ethyl alcohol is prepared in a suitable flask, provided with a stirrer, a refrigerating column and a charging funnel. The mixture is heated to reflux under stirring and the gradual addition of a solution comprising 3.08 g ($2.10^{-2}$ moles) of 2,4-dihydroxy-benzoic acid in a sufficient amount of ethyl alcohol is started. The mixture is kept boiling for 1 hour and, in the meanwhile, about 50 mls of $CHCl_3$ are added, so as to obtain a homogeneous solution.

The mixture is then concentrated to a small volume under reduced pressure and the precipitation of the salt is completed by diluting with diethyl ether. Then the filtering in a Buchner filter and the drying in an aerated furnace at 50° C. are carried out.

10 g of a crystalline product are obtained, it being soluble in ethyl alcohol and having melting point of 160°–170° C. The content of vincamine in the salt is 69%.

2.b

Apovineamine 2,4-dihydroxy-benzoate

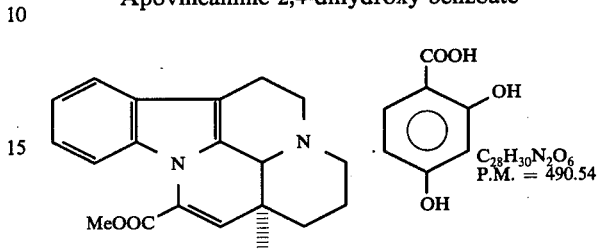

6.73 g ($2.10^{-2}$ moles) of apovincamine are dissolved in 100 mls of ethyl alcohol and then supplemented with 3.08 g ($2.10^{-2}$ moles) of resorcylic acid (2.4-dihydroxybenzoic acid) dissolved in the minimum amount of ethanol.

The mixture is boiled to reflux for 1 hour and then concentrated to a small volume.

The precipitation of the product is completed by adding diethyl ether and cooling in an ice bath.

The filtering on a Buchner filter and the drying at 50° C. in an aerated furnace are carried out, thus obtaining 9.6 g of a product having a melting point of 170°–173° C., which is soluble in alcohol but not in water and in the common organic solvents. The content of the apovincamine in the salt is 65%.

EXAMPLE 3

3.a

Vincamine glucose-1-phosphate

[structure]

$C_{48}H_{65}N_4O_{15}P$
P.M. = 969

5.5 g of vincamine are suspended in a mixture of 250 mls of ethyl alcohol and 35 mls of $CHCl_3$. The mixture is heated to 70° C. in a water bath under stirring and dropwise supplemented with an aqueous solution containing 2 g of glucose-1-phosphate.

The mixture is maintained under stirring at 70° C. for 30 minutes and then concentrated to a small volume under reduced pressure. It is then taken with 2 × 200 mls of ethanol, the mixture being thereafter concentrated to a final volume of 80 mls.

The vincamine excess which separates is filtered and the filtrate is concentrated to 40 mls.

The solution is diluted until it becomes cloudy, and then it is left on standing for the crystallization at room temperature. After filtration and drying in an aerated furnace at 60° C., 5.2 g of vincamine glucose-1-phosphate are obtained, as a white crystalline solid product, which is partially soluble in water and has a melting point of 210° C. (with.dec.).

The content of vincamine in the salt is 70.3%.

3.b

Apovincamine glucose-1-phosphate

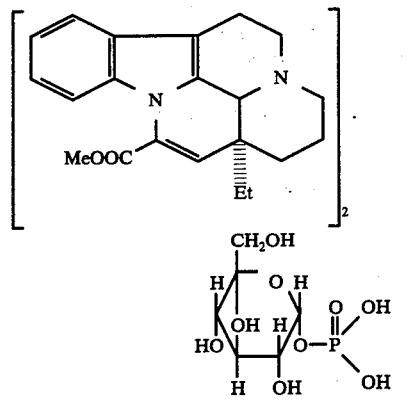

$C_{48}H_{61}N_4O_{13}P$
P.M. = 933

The process of the example 3.a is repeated, except that 6.7 g of apovincamine and 2.6 g of glucose-1-phosphate are used.

6.25 g are obtained of a white crystalline product, soluble in water and having melting point of 155° C. (with dec.).

The content of vincamine in the salt is 70%.

EXAMPLE 4

4.a

Vincamine glucose-1-phosphate, acid salt

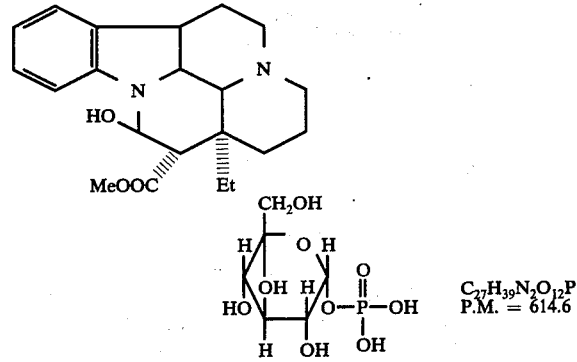

$C_{27}H_{39}N_2O_{12}P$
P.M. = 614.6

The procedure of the example 3.a is repeated, except that 3.8 g of vincamine and 3.1 g of glucose-1-phosphate are used.

5.8 g are obtained of a white crystalline product, soluble in water and having melting point of 172° C.

The content of vincamine in the salt is 58.6%.

4.b

Apovincamine glucose-1-phosphate, acid salt

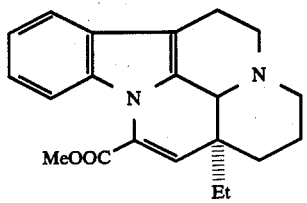

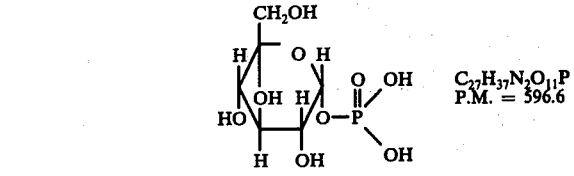

$C_{27}H_{37}N_2O_{11}P$
P.M. = 596.6

This compound is prepared according to the method of the preceding example, starting from 4.3 g of glucose-1-phosphate and 5.56 g of apovincamine.

5.7 g are obtained of a white, crystalline, water soluble, solid product, having melting point of 162° C. (with dec.).

The corresponding salts and adducts of vincamine and apovincamine with glucose-6-phosphate are obtained in the identical manner as that already disclosed in the examples for the glucose1-phosphate.

EXAMPLE 5

5.a

Vincamine 2,6-dihydroxybenzoate

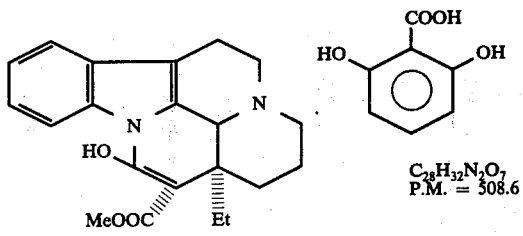

$C_{28}H_{32}N_2O_7$
P.M. = 508.6

A suspension of 7.08 g ($2.10^{-2}$ moles) of vincamine in 100 mls of ethyl alcohol is heated to reflux under stirring and gradually supplemented with a solution of 3.08 g ($2.10^{-2}$ moles) of 2,6-dihydroxybenzoic acid in a sufficient amount of ethanol. The mixture is maintained under boiling for about 1 hour and simultaneously 50 mls of $CHCl_3$ are added, so as to obtain a homogeneous solution. The mixture is concentrated under reduced pressure to a small volume and the precipitation of the salt is completed by diluting with diethyl ether.

The mixture is filtered on a Buchner filter and dried in an aerated furnace at 50° C.

10 g are obtained of an amorphous product, which is insoluble in water and alcohol. The content of vincamine in the salt is 74.6%.

5.b

Apovincamine 2,6-dihydroxybenzoate

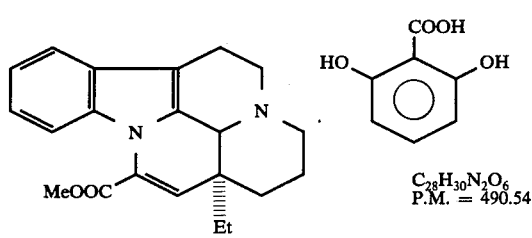

This salt is prepared according to the preceding example 5.a, starting from 3.37 g ($10^{-2}$ moles) of apovincamine and 1.54 g ($10^{-2}$ moles) of 2,6-dihydroxybenzoic acid.

4.8 g are obtained of a product having melting point of 145° C., which is insoluble in water and poorly soluble in alcohol. The content of apovincamine in the salt is 69.6%.

EXAMPLE 6

6.a

Vincamine 2,5-dihydroxybenzoate

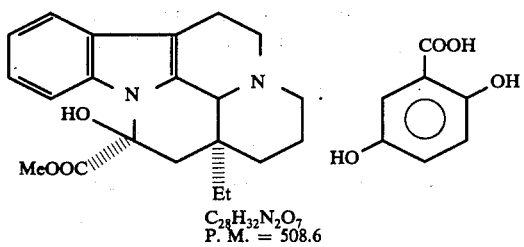

By repeating the Example 5a., starting from 7.08 g ($2.10^{-2}$ moles) of vincamine and 3.08 g ($2.10^{-2}$ moles) of 2,5dihydroxybenzoic acid, 10 g are obtained of an amorphous product, insoluble in water and in alcohol, having a vincamine content of 69%.

6.b

Apovincamine 2,5-dihydroxybenzoate

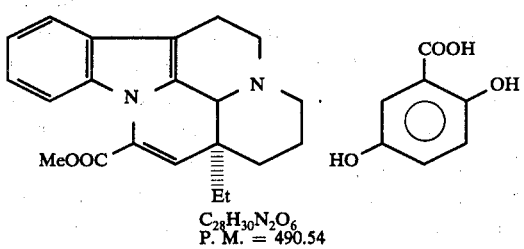

Like the preceding examples, starting from 3.37 g ($10^{-2}$ moles) of apovincamine and from 1.54 g ($10^{-2}$ moles) of 2,5-dihydroxybenzoic acid, there are obtained 4.8 g of a product insoluble in water and alcohol, having melting point of 120°-130° C. and a content of apovincamine of 64%.

EXAMPLE 7

7.a

Vincamine 3,5-dihydroxybenzoate

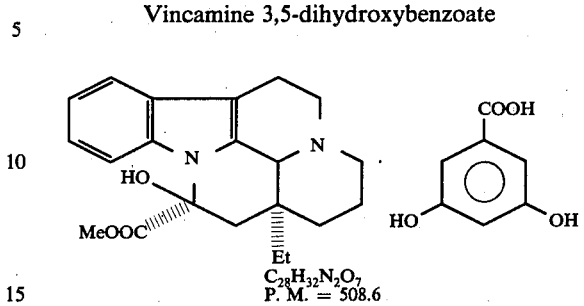

According to the method of the precedng examples and starting from 7.08 g ($2.10^{-2}$ moles) of vincamine and 3.08 g ($2.10^{-2}$ moles) of 3,5-dihydroxybenzoic acid, there are obtained 10 g of a salt in form of an amorphous substance, insoluble in water and alcohol.

The content of vincamine of the salt is 67.4%.

7.b

Apovincamine 3,5-dihydroxybenzoate

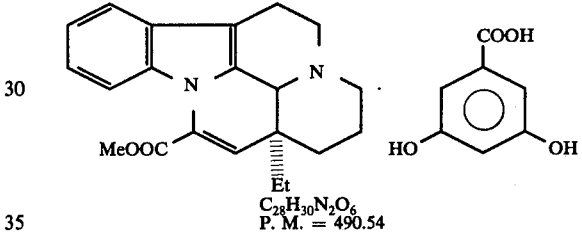

Like the preceding examples, this product is prepared from 3.37 g of apovincamine and 1.54 g of 3,5-dihydroxybenzoic acid.

There are obtained 4.8 g of the salt having melting point of 220° C., insoluble in water and soluble in alcohol. The apovincamine content is 53%.

EXAMPLE 8

8.a

Vincamine p-toluensulfonate

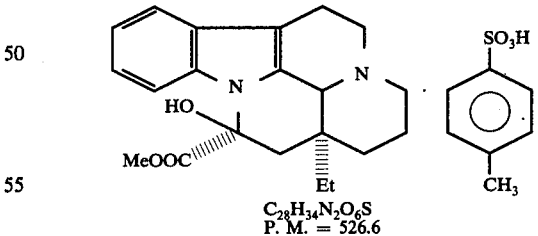

7.08 g ($2.10^{-2}$ moles) of vincamine are suspended in 100 mls of anhydrous methanol. The suspension is heated in a water bath to 60° C. and a solution of 3.8 g ($2.10^{-2}$ moles) of p-toluen-sulfonic acid monohydrate in 30 mls of ethanol are added.

At the end of the addition a clear, slightly yellow solution is obtained. It is maintained for 15 minutes under slow stirring at 60° C. and then concentrated under normal pressure to a dry residue.

The solid is taken with a mixture comprising 5 mls of ethanol and 20 mls of diethyl ether and crystallized at room temperature. The mixture is filtered, dried at 60° C. in an aerated furnace and there are obtained about 9.5 g of a solid, crystalline product, soluble in water and in alcohol, having melting point of 204°–212° C.

The vincamine content of the salt is 67%.

8.b

Apovincamine p-toluensulfonate

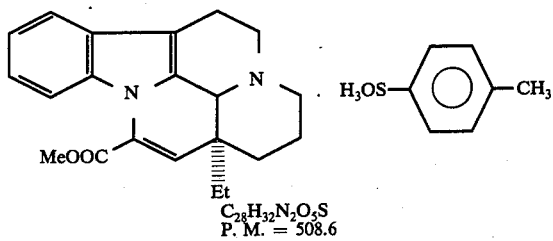

According to the method of the example 8.a the salt is prepared from 3.36 g ($10^{-2}$ moles) of apovincamine and 1.72 g ($10^{-2}$ moles) of anhydrous p-toluensulfonic acid. There are obtained 4.3 g of the salt, which is soluble in alcohol, insoluble in water, with a melting point of 150° C. and an apovincamine content of 60%.

EXAMPLE 9

9.a

Vincamine clofibrate
(2-(p-chlorophenoxy)-2-methylpropionate)

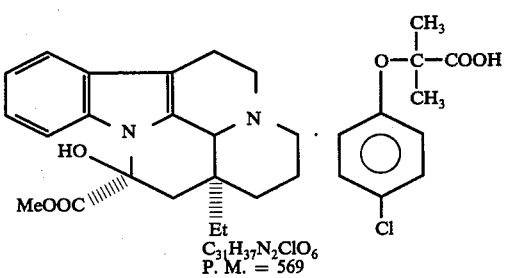

This product is prepared according to the method of the example 5.a, by using 4.29 g ($2.10^{-2}$ moles) of clofibric acid (2-(p-chlorophenoxy)-2-methylpropionic acid) and 7.08 g ($2.10^{-2}$ moles) of vincamine.

There are obtained 11 g of the salt, soluble in alcohol and insoluble in water, having melting point of 195° C. The vincamine content of the salt is about 60%.

9.b

Apovincamine clofibrate

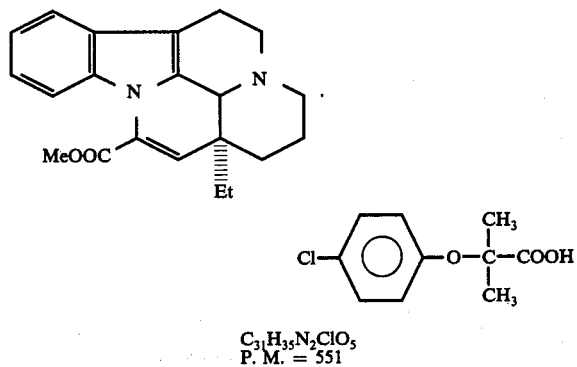

The preceding example is repeated starting from 3.36 g of apovincamine and 2.14 g of clofibric acid. The final product (3.5 g) is a low melting solid, m.p. 65° C., which is insoluble in water and soluble in alcohol, with an apovincamine content of 61%.

EXAMPLE 10

10.a

Vincamine pivalate (trimethylacetate)

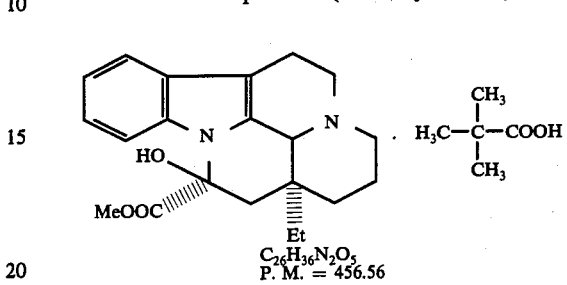

This salt is prepared, like the examples 5 and 9, starting from 2.41g($2.10^{-2}$ moles) of pivalic acid and 7.08 g ($2.10^{-2}$ moles) of vincamine. There are obtained 9 g of a solid substance, insoluble in water and in alcohol, having melting point of 235° C. The vincamine content in the salt is 70%.

10.b

Apovincamine pivalate

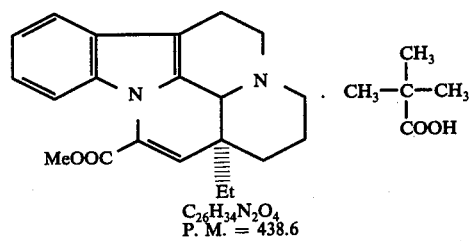

According to the method of the preceding example, 4 g of the salt are prepared starting from 1.02 g of pivalic acid and 3.36 g of apovincamine. The product has melting point of 110° C., is insoluble in water and soluble in alcohol; the apovincamine content thereof is 73.8%.

EXAMPLE 11

11.a

Vincamine 4-acetamidobutyrate

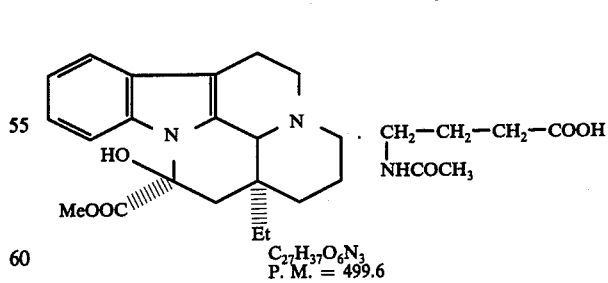

This salt is prepared starting from a mixture of alcohol and chloroform as for the salt of the example 1, starting from 2.9 g of 4-acetamidobutyric acid ($2.10^{-2}$ moles) and 7.08 g ($2.10^{-2}$ moles) of vincamine, there are obtained 9 g of a product, insoluble in water and alcohol, having melting point of 210° C. The vincamine content of the salt is 70%.

11.b

Apovincamine 4-acetamidobutyrate

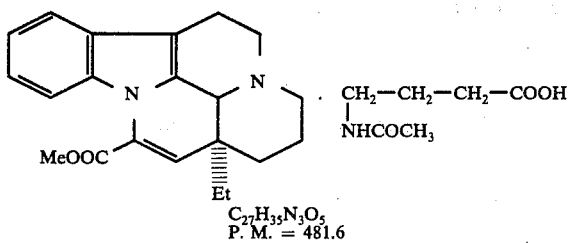

$C_{27}H_{35}N_3O_5$
P. M. = 481.6

According to the method of the preceding example, there are obtained, starting from 3.36 g of apovincamine and 1.45 g of 4-acetamidobutyric acid, 4.4 g of a product, having melting point of 128° C. and insoluble in water and alcohol. The apovincamine content of the salt is 56%.

EXAMPLE 12

12.a

Vincamine furoate (furan-2-carboxylate)

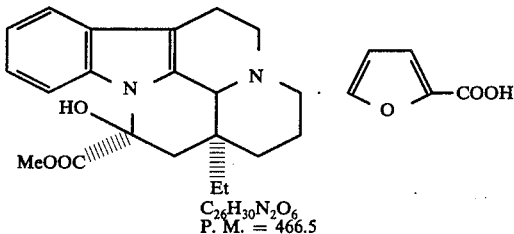

$C_{26}H_{30}N_2O_6$
P. M. = 466.5

7.08 g of vincamine are suspended in 100 mls of hot ethyl alcohol, at 60°–70° C. and, under stirring, a solution of 2-furoic acid in alcohol is slowly added, the mixture being then refluxed for 1 hour. It is advisable to add 40–50 mls of chloroform in order to obtain a homogeneous solution.

The reaction mixture is then concentrated to a dry residue, and the product is ground and dried in an aerated furnace. There are obtained 9.3 g of a substance, insoluble in water and alcohol, having a vincamine content of 74%.

12.b

Apovincamine furoate

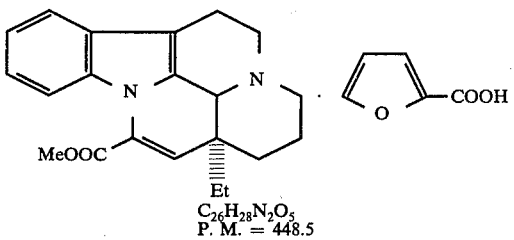

$C_{26}H_{28}N_2O_5$
P. M. = 448.5

By repeating the preceding example, there are obtained 8.2 g of the salt from 6.73 g (2.10⁻² moles) of apovincamine and 2.24 g (2.10⁻² moles) of furan-2-carboxylic acid. The product has a melting point of about 120° C. is insoluble in water and soluble in alcohol; the apovincamine content thereof is 66%.

EXAMPLE 13

13.a

Vincamine D(+)-camphorsulfonate

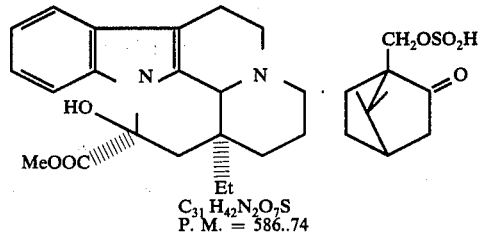

$C_{31}H_{42}N_2O_7S$
P. M. = 586..74

5 g (2.10⁻² moles) of D(+)-camphorsulfonic acid monohydrate are dissolved in 15 mls of ethanol, and the solution is added to a suspension of 7.08 g (2.10⁻² moles) of vincamine in 90 mls of ethanol at 70° C. under stirring.

A homogeneous solution is obtained, which is maintained at 70° C. for 10–15 minutes. The mixture is then concentrated to a volume of 20–25 mls and crystallized in an ice bath. The mixture is filtered, washed on the filter with a very small amount of cold alcohol, and dried in an aerated furnace at 60° C. There are obtained about 11 g of a product having a melting point of 228°–230° C., soluble in water, poorly soluble in alcohol and insoluble in the common organic solvents.

The vincamine content is 61%.

13.b

Apovincamine D(+)-camphorsulfonate

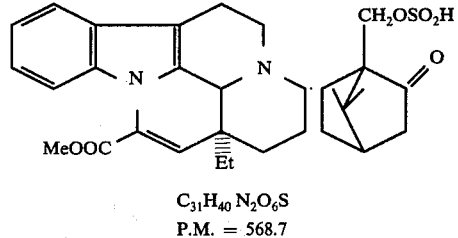

$C_{31}H_{40}N_2O_6S$
P.M. = 568.7

According to the same method of the example 13.a, starting from 6.73 g of apovincamine and 4.64 g of D(+)-camphorsulfonic acid, there are obtained 10.6 g of the salt, having melting point of about 258° C., which is soluble in water and alcohol and has an apovincamine content of 53%.

EXAMPLE 14

14.a

Vincamine L(+)-O,O-dibenzoyltartrate

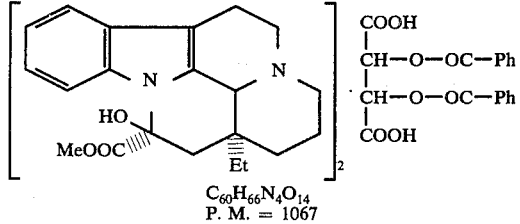

$C_{60}H_{66}N_4O_{14}$
P. M. = 1067

3.76 g (2.10⁻² moles) of L(+)-O,O-dibenzoyltartaric acid, monohydrate, are dissolved in 40 mls of ethanol and the resulting solution is added to a suspension of 7.08 g ($2.10^{-2}$ moles) of vincamine in 200 mls of alcohol at 70° C. The mixture is maintained in the hot condition and under stirring for 20 minutes and then the solution is concentrated to a final volume of 25–30 mls. The precipitation is completed in an ice bath. The mixture is filtered, washed with a very small amount of cold alcohol and dried in an aerated furnace at 60° C. There are obtained about 10 g of a product, m.p. 210° C., which is poorly soluble in water and alcohol and insoluble in the common solvents. The content of vincamine of the salt is 60%.

14.b

Apovincamine L(+)-O,O-dibenzoyltartrate

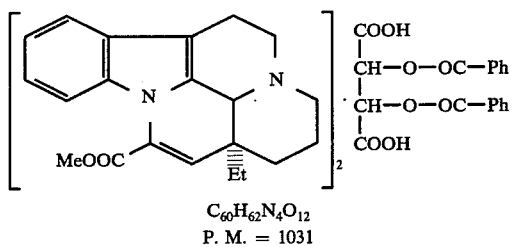

$C_{60}H_{62}N_4O_{12}$
P. M. = 1031

According to the method of the preceding example, starting from 1.8 g of dibenzoyltartaric acid and 3.37 g of apovincamine, there are obtained 5.1 g of a salt soluble in alcohol, with a melting point of 120° C. and an apovincamine content of 53%

EXAMPLE 15

15.b

Apovincamine nicotinate

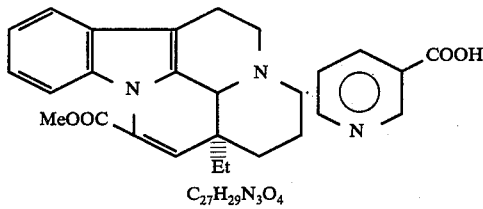

$C_{27}H_{29}N_3O_4$

P. M. = 459.5

2.46 g ($2.10^{-2}$ moles) of nicotinic acid are suspended in 30 mls of ethanol and the mixture is added to a solution of 6.73 g ($2.10^{-2}$ moles) of apovincamine in 80 mls of ethanol and 60 mls of chloroform. The mixture is maintained at 70° C. under stirring for 10–15 minutes and then concentrated to 15–20 mls, the precipitation being completed at room temperature. Then the mixture is filtered and dried in a furnace at 60° C.

There are obtained 8.7 g of a product having melting point of 135° C., which is insoluble in water and alcohol, with an apovincamine content of 86.5%.

EXAMPLE 16

16.a

Vincamine acetylsalicylate

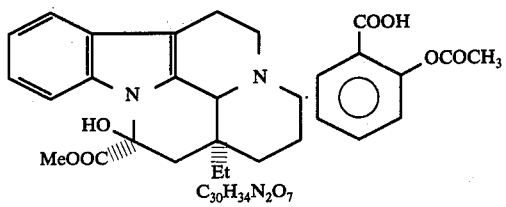

$C_{30}H_{34}N_2O_7$

A solution of 3.6 g ($2.10^{-2}$ moles) of acetylsalicylic acid in 30 mls of ethanol is added to a solution of 7.08 g ($2.10^{-2}$ moles) of vincamine in 80 mls of ethanol and 60 mls of $CHCl_3$. The mixture is maintained under stirring at 70° C. for 10 minutes and then concentrated to 60 mls. The residue is taken with ethanol (70 mls) and the solvent is evaporated to a final volume of 15 mls.

The precipitation is completed with 10 mls of ether, by cooling in an ice bath, and the mixture is filtered, washed onto the filter with ether and dried in a furnace at 60° C.

There are obtained 10 g of a product having undefined melting point and poorly soluble in all the common solvents. The vincamine content is 61%.

16.b

Apovincamine acetylsalicylate

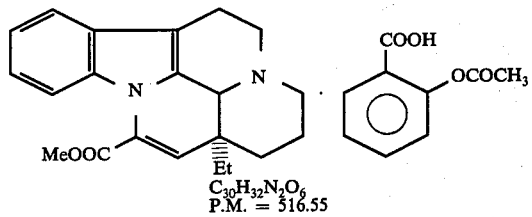

$C_{30}H_{32}N_2O_6$
P.M. = 516.55

By repeating the preceding example, starting from 1.8 g of acetylsalicylic acid and 3.36 g of apovincamine, there are obtained 4.1 g of a salt having melting point of about 120° C., which is soluble in alcohol, very little soluble in water and with an apovincamine content of 75.3%.

EXAMPLE 17

17.a

Vincamine methylsulfate

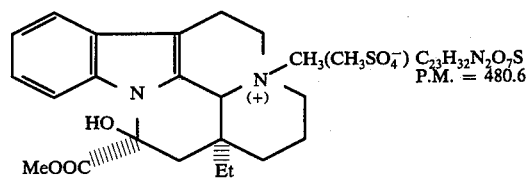

$C_{23}H_{32}N_2O_7S$
P.M. = 480.6

7.08 g ($2.10^{-2}$ moles) of vincamine are dissolved in 900 mls of boiling anhydrous acetone. Under stirring, 1.8 mls of dimethylsulfate are added and the resulting mixture is maintained under boiling for 6 hours. The mixture is concentrated to 400 mls and maintained on standing for a night. The mixture is filtered, washed onto the filter with ether and dried in a vacuum furnace at 50° C. There are obtained 7 g of a product having melting point of 191° C., soluble in water and alcohol.

17.b

Apovincamine methylsulfate

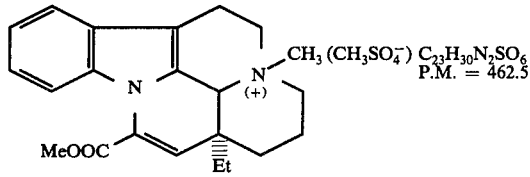

7.3 g of salt are prepared, likewise the preceding example, starting from 6.73 g ($2.10^{-2}$ moles) of apovincamine and from about 2 mls of dimethyl sulfate. The final product has a melting point of 280° C. and is water soluble but poorly soluble in alcohol.

EXAMPLE 18

18.a

Vincamine enanthate

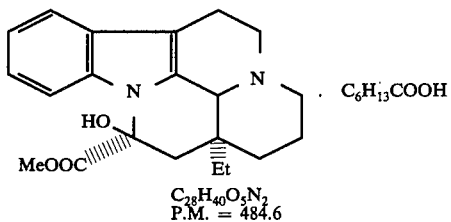

The preparation is carried out according to the example 15, starting from 7.08 g ($2.10^{-2}$ moles) of vincamine and from 2.61 g ($2.10^{-2}$ moles) of enanthic (n-heptanoic) acid. There are obtained about 10 g of a semi-solid product, insoluble in the common solvents. The vincamine content is 66.5%.

18.b

Apovincamine enanthate

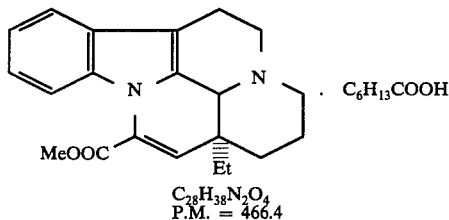

According to the preceding example, 8.3 g of the salt are obtained starting from 6.73 g of apovincamine and 2.61 g of enanthic acid. The substance is insoluble in water and alcohol and the apovincamine content is 73%.

EXAMPLE 19

19.a

Vincamine p-chlorophenoxyacetate

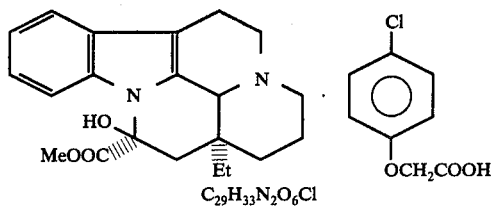

This preparation is carried out, likewise the preceding example, from 7.08 g ($2.10^{-2}$ moles) of vincamine and 3.73 g ($2.10^{-2}$ moles) of p-chlorophenoxyacetic acid. There are obtained 9.6 g of an amorphous product, soluble in alcohol and insoluble in water and in the common organic solvents. The vincamine content is 64.7%

19.b

Apovincamine p-chlorophenoxyacetate

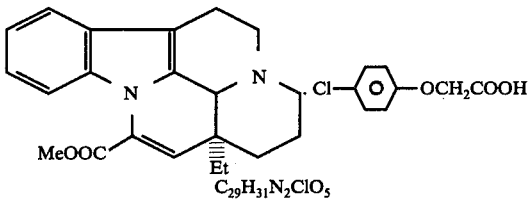

4 g of the salt are prepared, according to the method of the example 19.a, starting from 3.36 g of apovincamine and 1.86 g of p-chlorophenoxyacetic acid. The melting point of the salt is about 120° C. and it is insoluble in water; the content of apovincamine is 64%.

EXAMPLE 20

20.a

Vincamine theophylline-7-acetate

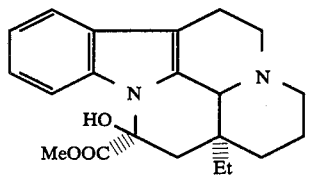

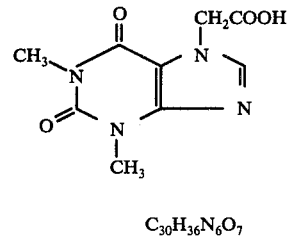

The salt is prepared, likewise the preceding examples, from 7.08 g ($2.10^{-2}$ moles) of vincamine and 4.77 g ($2.10^{-2}$ moles) of theophylline-7-acetic acid. There are obtained 12 g of a crystalline product having melting point of 188° C., which is soluble in alcohol and insoluble in water and in the common organic solvents.

20.b

Apovincamine theophylline-7-acetate

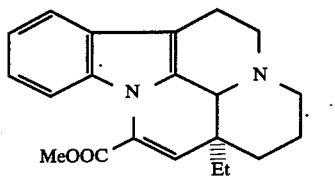
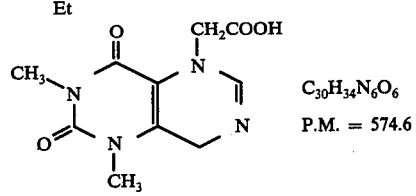

C$_{30}$H$_{34}$N$_6$O$_6$
P.M. = 574.6

This salt is prepared, according to the method of the preceding example, from 3.36 g (10$^{-2}$ moles) of apovincamine and 2.38 g (10$^{-2}$ moles) of theophylline-7-acetic acid.

There are obtained 5.4 g of an amorphous substance, soluble in water, with an apovincamine content of 50%

EXAMPLE 21

21.a

Vincamine caproate

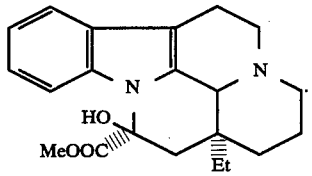 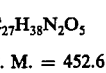

C$_6$H$_{12}$O$_2$
C$_{27}$H$_{38}$N$_2$O$_5$
P. M. = 452.6

7.08 g (2.10$^{-2}$ moles) of vincamine and 2.32 g (2.10$^{-2}$ moles) of caproic acid are reacted according to the same method of the preceding example. There are obtained 8.2 g of an oily substance, insoluble in water and in the common solvents. The vincamine content is 67%.

21.b

Apovincamine caproate

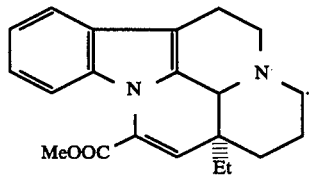 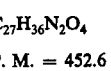

C$_6$H$_{12}$O$_2$
C$_{27}$H$_{36}$N$_2$O$_4$
P. M. = 452.6

As in the preceding example, from 3.36 g of apovincamine and 1.17 g of caproic acid, there are obtained 4.1 of a semi-solid product, having low melting point, insoluble in water and alcohol, and with an apovincamine content of 71%

EXAMPLE 22

22.a

Vincamine caprate

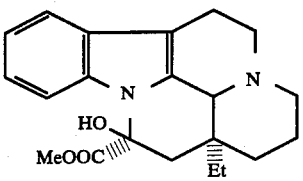 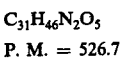

· C$_{10}$H$_{20}$O$_2$  C$_{31}$H$_{46}$N$_2$O$_5$
P. M. = 526.7

From 7.08 g (2.10$^{-2}$ moles) of vincamine and 3.45 g (2.10$^{-2}$ moles) of capric acid, there are obtained 10 g of an oily, semi-solid substance, insoluble in water and in the common organic solvents. The vincamine content is 65.3%.

22.b

Apovincamine caprate

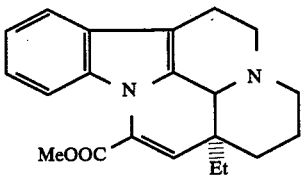 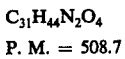

· C$_{10}$H$_{20}$O$_2$  C$_{31}$H$_{44}$N$_2$O$_4$
P. M. = 508.7

According to the preceding example, 4.5 g of the salt are prepared, starting from 3.36 g (10$^{-2}$ moles) of apovincamine and 1.72 g (10$^{-2}$ moles) of capric acid. The product is a semisolid, low melting substance, insoluble in water and alcohol, with an apovincamine content of 50%.

EXAMPLE 23

23.a

Vincamine alginate 7.08 g (2.10$^{-2}$ moles) of vincamine and 4.75 g (2.10$^{-2}$ equivalents) of alginic acid are reacted according to the method of the preceding examples. For determining the acid equivalent number of the alginic acid (polymannuronic acid), 1.00 g of alginic acid are dissolved in 50.00 mls of 0.1N NaOH. The excess alkalinity is titrated with 8.00 mls of 0.1N HCL. Thus 4.2 × 0.1 = 4.2 meq of alginic acid/gram of substance neutralize 1.49 g. of vincamine as a base.

There are obtained 10.5 g of a product having melting point of 280° C., which is insoluble in water and in the common organic solvents. The vincamine content is 56.6%.

23.b

Apovincamine alginate

By operating according to the method of the preceding example, 4.7 g of adduct are obtained starting from 3.36 g of apovincamine and 2.37 g of alginic acid. The product decomposes at 198° C., is insoluble in water and alcohol and the apovincamine content thereof is 48%.

EXAMPLE 24

24.a

Vincamine tannate

This compound is prepared from 3.54 g of vincamine, as a free base, and from 17 g of tannic acid according to the method of the preceding examples. There are obtained 19 g of an amorphous alcohol soluble product. The vincamine content is 18.6%.

24.b

Apovincamine tannate

Starting from 3.36 g of apovincamine and from 17 g of tannic acid, by operating according to the preceding example, there are obtained 18 g of the adduct, which is insoluble in water and has an apovincamine content of 16%.

EXAMPLE 25

25.a

Vincamine (D,L)-mandelate

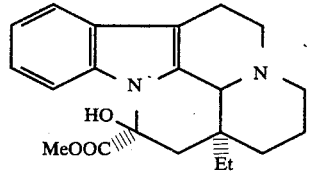

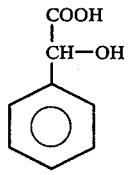

$C_{29}H_{34}N_2O_6$
P. M. = 506.6

This salt is prepared from 7.08 g ($2.10^{-2}$ moles) of vincamine and from 3.05 g ($2.10^{-2}$ moles) of (D,L)-mandelic acid, according to the method of the example 15.a. There are obtained 10 g of a substance having melting point of 210° C., which is soluble in alcohol and insoluble in water and in the common organic solvents. The vincamine content is 55.64%.

25.b

Apovincamine (D,L)-mandelate

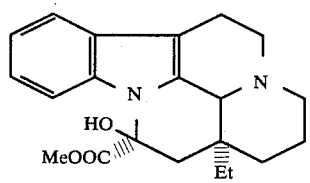

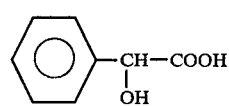

$C_{29}H_{32}N_2O_5$
P. M. = 488.54

According to the same method of the preceding example, starting from 3.36 g of apovincamine and from 1.52 g of (D,L)-mandelic acid, there are obtained 4.3 g of salt having melting point of 72° C., which is soluble in alcohol and insoluble in water. The apovincamine content in the salt is 69.7%.

EXAMPLE 26

26.a

Vincamine indolyl-3-acetate

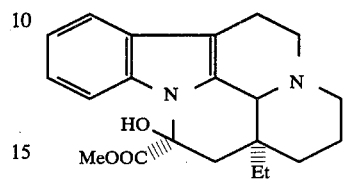

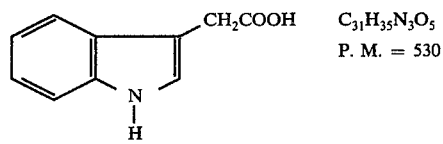

$C_{31}H_{35}N_3O_5$
P. M. = 530

This preparation is carried out starting from 7.08 g ($2.10^{-2}$ moles) of vincamine, as the free base, and from 3.54 g ($2.10^{-2}$ moles) of indolyl-3-acetic acid, according to the method of the preceding examples.

There are obtained 10.5 g of an amorphous product, which is insoluble in water and in the common solvents. The vincamine content is 63%.

26.b

Apovincamine indolyl-3-acetate

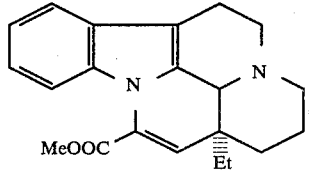

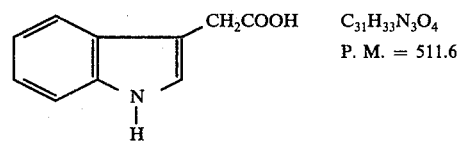

$C_{31}H_{33}N_3O_4$
P. M. = 511.6

4.7 g of the salt are prepared from 3.36 g of apovincamine and 1.75 g of indolyl-3-acetic acid, according to the method of the preceding example. The product having melting point of 132° C., is insoluble in water and poorly soluble in alcohol; the apovincamine content thereof is 61%.

EXAMPLE 27

27.a

Vincamine hydroquinone

This adduct is prepared in an equimolar ratio from 7.08 g ($2.10^{-2}$ moles) of vincamine and 2.2 g ($2.10^{-2}$ moles) of hydroquinone. The product is insoluble in water and in the common organic solvents; the vincamine content thereof is 77.3%.

27.b

Apovincamine hydroquinone

This adduct is prepared in an equimolar ratio from 3.36 g of apovincamine and 1.1 g of hydro-quinone (or hydrochinone).

There are obtained 3.4 g of adduct which is soluble in alcohol and insoluble in water, with a melting point of 122° C. and an apovincamine content of 72.3%.

EXAMPLE 28

28.a

Vincamine salicylate

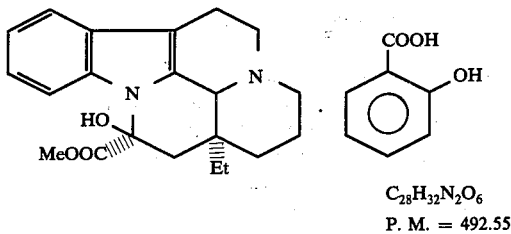

$C_{28}H_{32}N_2O_6$
P. M. = 492.55

The salt is prepared, according to the method of the example 15, starting from 2.77 g ($2.10^{-2}$ moles) of salicylic acid and 7.08 g ($2.10^{-2}$ moles) of vincamine. There are obtained 9.5 g of the product having melting point of 120° C., which is soluble in alcohol and insoluble in water and in the common organic solvents. The vincamine content is 53.5%.

28.b

Apovincamine salicylate

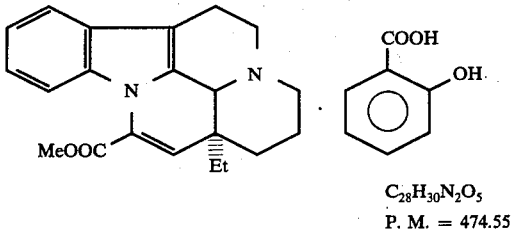

$C_{28}H_{30}N_2O_5$
P. M. = 474.55

The preceding example is repeated, starting from 1.39 g of salicylic acid and from 3.36 g of apovincamine; there are obtained 3.9 g of the salt having a melting point of 110° C., soluble in alcohol and having an apovincamine content of 77.6%.

EXAMPLE 29

29.A

Vincamine dihydroxyphenylalanine (DOPA)

This product is prepared starting from 7.08 g ($2.10^{-2}$ moles) of vincamine and 3.91 g ($2.10^{-2}$ moles) of dihydroxyphenylalanine (DOPA).

There are obtained 10.8 g of a substance having melting point of 235° C., which is practically insoluble in water and in the common organic solvents. The vincamine content is 65%.

29.b

Apovincamine dihydroxyphenylalanine

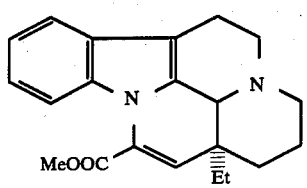

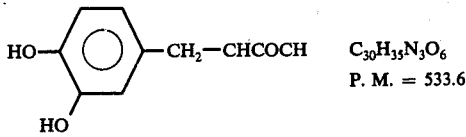

$C_{30}H_{35}N_3O_6$
P. M. = 533.6

According to the method of the preceding example and starting from 6.73 g of apovincamine and 3.94 g of dihydroxyphenylalanine, there are obtained 9.7 g of an amorphous insoluble adduct, with an apovincamine content of 58.3%.

EXAMPLE 30

30.a

Vincamine pectin (1:1 adduct)

This product is obtained by admixing 7.08 g of vincamine and 7.08 g of pectin (methyl polygalacturonate) in a mixture of alcohol and chloroform. The resulting solution or partial suspension is concentrated to a residue. The residue is ground and dried in an aerated furnace at 60° C.

There are obtained about 14 g of a product having melting point of about 235° C., which is insoluble in water and in the common organic solvents.

30.b

Apovincamine-pectin (1:1 adduct)

From 6.73 g of apovincamine and 6.73 g of pectin there are obtained 12.2 g of an adduct having melting point of 163° C. and little soluble in alcohol. The apovincamine content is 50%.

EXAMPLE 31

31.a

Vincamine-pectin (2:1 adduct)

This product is prepared from 7.08 g of vincamine and 3.54 g of pectin, according to the method of the example 30.a. There are obtained 10.5 g of adduct having melting point of about 228°-235° C., which is practically insoluble in water and in the common organic solvents.

31.b

Apovincamine-pectin (2:1 adduct)

Starting from 6.73 g of apovincamine and 3.36 g of pectin, there are obtained 9.4 g of the adduct having melting point of 165° C., which is insoluble in water and poorly soluble in alcohol, with an apovincamine content of 63%.

For the compounds of the present invention a number of pharmacological and pharmacokinetic tests have been carried out. In the following Table 1 the values of the LD50 per intraperitoneal route are reported, thus demonstrating that the subject compounds have a relatively low toxicity. As regards the pharmacological and pharmacodynamic activity, it has been studied on the percent variations of the hematic flow, as recorded at the vertebral arteria in the dog after administration of the tested compounds. As regards the pharmacokinetic tests, the compounds were administered per oral route to the Wistar rat, and the hematic levels at different times from the administration were measured. The results demonstrated that not only the therapeutical properties as possessed by vincamine and apovincamine respectively were maintained, but also that, in a more or less relevant degree, the compounds of the present invention show a prolonged effect.

TABLE 1

|  | Ex. N° | $LD_{50}$ mg/kg i.p. | Toxicity (Gleason) |
|---|---|---|---|
| Vincamine HCl | — | 800 | modest |
| Apovincamine | — | 2000 | negligible |
| Glucose-1-phosphate disodium | 1.a | 2000 | " |
| " | 1.b | 2000 | " |
| 2,4-dihydroxybenzoate | 2.a | 750 | modest |
| " | 2.b | 650 | modest |
| Glucose-1-phosphate | 3.a | 1150 | light |
| " | 3.b | 850 | modest |
| Glucose-1-phosphate acid salt | 4.a | 700 | modest |
| " | 4.b | 600 | modest |
| 2,6-dihydroxybenzoate | 5.a | 550 | modest |
| " | 5.b | 750 | modest |
| 2,5-dihydroxybenzoate | 6.a | 800 | modest |
| " | 6.b | 750 | modest |
| 3,5-dihydroxybenzoate | 7.a | 850 | modest |
| " | 7.b | 750 | modest |
| p-toluenesulfonate | 8.a | 1250 | light |
| " | 8.b | 900 | modest |
| clofibrate | 9.a | 900 | modest |
| " | 9.b | 800 | light |
| pivalate | 10.a | 1300 | light |
| " | 10.b | 750 | modest |
| 4-acetamidobutyrate | 11.a | 700 | modest |
| " | 11.b | 1500 | light |
| furoate | 12.a | 800 | modest |
| " | 12.b | — | — |
| D(+)camphorsulfonate | 13.a | 1350 | light |
| " | 13.b | — | — |
| L(+)-O,O-dibenzoyltartrate | 14.a | 950 | modest |
| " | 14.b | 1500 | light |
| nicotinate | 15.a | 900 | modest |
| " | 15.b | 750 | modest |
| acetylsalicylate | 16.a | 900 | modest |
| " | 16.b | 750 | modest |
| enanthate | 18.a | 750 | modest |
| " | 18.b | 1500 | light |
| p-chlorophenoxyacetate | 19.a | 750 | modest |
| " | 19.b | 750 | modest |
| theophylline-7-acetate | 20.a | 700 | modest |
| " | 20.b | — | — |
| caproate | 21.a | 900 | modest |
| " | 21.b | 1900 | light |
| caprate | 22.a | 2000 | negligible |
| " | 22.b | 1900 | light |
| alginate | 23.a | 550 | modest |
| " | 23.b | 750 | modest |
| tannate | 24.a | 700 | modest |
| " | 24.b | — | — |
| (D,L)-mandelate | 25.a | 900 | modest |
| " | 25.b | — | — |
| indolyl-3-acetate | 26.a | 1000 | modest |
| " | 26.b | 750 | modest |
| hydroquinone | 27.a | 500 | modest |
| " | 27.b | 750 | modest |
| salicylate | 28.a | 700 | modest |
| " | 28.b | 750 | modest |
| dihydroxyphenylalanine | 29.a | 1500 | light |
| " | 29.b | 900 | light |
| pectin (1 : 1) | 30.a | 2000 | negligible |
| " | 30.b | 750 | modest |
| pectin (2 : 1) | 31.a | 2000 | negligible |
| " | 31.b | 900 | light |
| glucose-6-phosphate disodium | 1.c | 2000 | negligible |
| " | 1.d | 2000 | negligible |
| " | 3.c | 1000 | light |
| " | 3.d | 900 | modest |
| glucose-6-phosphate acid salt | 4.c | 800 | modest |
| glucose-6-phosphate acid salt | 4.d | 700 | modest |

For the evaluation of the absorption, all the compounds have been orally administered at the dosage of 100 mg/kg, expressed as vincamine and apovincamine, in form of a suspension in a 5% carboxymethyl cellulose solution.

The absorption was determined by evaulating the hematic levels at the following times (minutes) : 0, 30, 120, 240, 480, 10 hours and 12 hours, in order also to assess the time from the administration (max conc.time) the maximum absorption occurred.

The vincamine and apovincamine concentrations were assessed by chromatographic method.

For the evaluation of the prolonged action of the salts and of the adducts of vincamine and apovincamine the following criterium was adopted; as derivatives having a long-acting effect, there are considered those which, 120 minutes after the administration, show hematic levels higher than those obtained with vincamine and apovincamine.

From the following Table 2 it is evident that the vincamine and apovincamine salts and adducts give place to the maximum hematic levels at times prevailingly and in great cases definitely higher than those of the vincamine HCl and of apovincamine, whereby an effect of the long-acting or prolonged type is confirmed.

The cerebral vasodilating activity was studied in the anestetized dog, by measuring, by means of Statham periarterial electromagnetic flowmeters, the hematic flow at the level of the cerebral arteria which, in such animal species, constitutes the greatest blood supply to the brain.

The compounds, when injected through the femoral vein at doses corresponding to 5 mg/kg of vincamine and apovincamine respectively, caused increases of the hematic flow directed to the brain at least comparable and some times even higher than those of the vincamine and apovincamine.

The resuls are reported in the TABLE 2 (last column) as the percent variations of the flow measured at the level of the ledt vertebral arteria after the i.v. administration of the several compounds to be tested to groups of 4 animals for each compound. The results also confirm that the compounds of the invention are all endowed with a vasodilating activity at the level of the cerebral circulus, such an action being, for some compounds, much more remarkable than that of vincamine and apovincamine.

TABLE 2

|  | Ex. N° | Max. conc. time (min.) | % increase |
|---|---|---|---|
| Vincamine HCl | — | 20 | 24.1 |
| Apovincamine | — | 60 | 25.6 |
| Glucose-1-phosphate disodium | 1.a | 480 | 27.3 |
| " | 1.b | 120 | 27.8 |
| 2,4-dihydroxybenzoate | 2.a | 120 | 24.8 |
| " | 2.b | 120 | 29.0 |
| Glucose-1-phosphate | 3.a | 240 | 29.0 |
| " | 3.b | 120 | 26.4 |
| Glucose-1-phosphate acid salt | 4.a | 240 | 26.6 |
| " | 4.b | 240 | 26.1 |
| 2,6-dihydroxybenzoate | 5.a | 120 | 23.6 |
| " | 5.b | 120 | 25.4 |
| 2,5-dihydroxybenzoate | 6.a | 120 | 28.0 |
| " | 6.b | 240 | 30.9 |
| 3,5-dihydroxybenzoate | 7.a | 240 | 26.3 |
| " | 7.b | 240 | 26.0 |
| p-toluenesulfonate | 8.a | 480 | 25.1 |
| " | 8.b | 480 | 29.0 |
| clofibrate | 9.a | 480 | 22.1 |
| " | 9.b | 480 | 28.3 |
| pivalate | 10.a | 240 | 27.9 |
| " | 10.b | 480 | 31.4 |
| 4-acetamidobutyrate | 11.a | 480 | 29.3 |

TABLE 2-continued

| Ex. N° | | Max. conc. time (min.) | % increase |
|---|---|---|---|
| " | 11.b | 480 | 33.0 |
| furoate | 12.a | 120 | 24.8 |
| " | 12.b | 240 | 24.0 |
| D(+)camphorsulfonate | 13.a | 60 | 30.1 |
| " | 13.b | 120 | 37.4 |
| L(+)-0,0-dibenzoyltartrate | 14.a | 60 | 29.6 |
| " | 14.b | 120 | 31.0 |
| nicotinate | 15.a | 60 | 21.9 |
| " | 15.b | 60 | 28.3 |
| acetylsalicylate | 16.a | 20 | 31.7 |
| " | 16.b | 60 | 40.1 |
| methylsulfate | 17.a | 60 | 28.4 |
| " | 17.b | 60 | 29.7 |
| enanthate | 18.a | 60 | 27.7 |
| " | 18.b | 120 | 33.1 |
| p-chlorophenoxyacetate | 19.a | 480 | 22.0 |
| " | 19.b | 480 | 28.4 |
| theophylline-7-acetate | 20.a | 60 | 24.5 |
| " | 20.b | 120 | 27.2 |
| caproate | 21.a | 20 | 30.0 |
| " | 21.b | 60 | 36.4 |
| caprate | 22.a | 120 | 23.9 |
| " | 22.b | 240 | 28.2 |
| Alginate | 23.a | 20 | 34.7 |
| " | 23.b | 60 | 38.0 |
| tannate | 24.a | 240 | 26.2 |
| " | 24.b | 480 | 29.8 |
| (D,L)-mandelate | 25.a | 20 | 39.4 |
| " | 25.b | 120 | 34.5 |
| indolyl-3-acetate | 26.a | 120 | 23.8 |
| " | 26.b | 120 | 28.7 |
| hydroquinone | 27.a | 120 | 29.1 |
| " | 27.b | 240 | 33.3 |
| salicylate | 28.a | 240 | 25.7 |
| " | 28.b | 240 | 26.7 |
| dihydroxyphenylalanine | 29.a | 20 | 38.2 |
| " | 29.b | 120 | 41.3 |
| pectin (1 : 1) | 30.a | 20 | 40.0 |
| " | 30.b | 60 | 39.6 |
| pectin (2 : 1) | 31.a | 240 | 24.9 |
| " | 31.b | 480 | 28.2 |
| Glucose-6-phosphate disodium | 1.c | 480 | 26.3 |
| " | 1.d | 120 | 29.3 |
| glucose-6-phosphate | 3.c | 240 | 28.4 |
| " | 3.d | 120 | 28.8 |
| glucose-6-phosphate acid salt | 4.c | 240 | 28.2 |
| " | 4.d | 240 | 30.0 |

On the basis of the above considerations it can be thus stated that the salts and adducts of the present invention can be used both per oral route and by parenteral route in order to obtain a pharmacological effect of the long-acting type.

CEREBRAL TROPISM

All the compounds were administered at the dose of 100 mg/kg, expressed as vincamine and apovincamine, as a suspension in a 5% carboxymethylcellulose solution.

The cerebral tropism was determined through the sacrifice of seven groups of three rats, at the times of 15 minutes, 30 minutes, 1 hour, 2 hours, 4 hours, 8 hours, after the administration, and by carrying out the measurement of the content of the subject compounds in the cerebral tissue by chromatographic method.

From the experimental results it is confirmed that the derivatives of the present invention show cerebral concentrations equal to or higher than those of vincamine and apovincamine, with a time behaviour consistent with the already mentioned prolonged effect, thus giving the evidence that the cerebral tropism of the vincamine and of the apovincamine is maintained and, in some cases, enhanced.

BLOOD PLATELET RESPIRATION

From the tests carried out in vivo in the rabbit it resulted that the compounds of the present invention are capable of enhancing the respiratory parameters of the blood platelets.

It is worth to point out that, through the administration of these compounds, it is possible to reduce the dosage of vincamine the therapeutical action being maintained or even improved.

In this connection it can be stated that for the pharmaceutical compositions containing, as the active ingredients, the compounds of the present invention, the following therapeutical dosages are foreseen:

(1) 40 - 120 mg/day for the derivatives of the vincamine;

(2) 40 - 160 mg/day for the derivatives of the apovincamine.

I claim:

1. A derivative of vincamine and apovincamine, having the therapeutical activity of these substances combined with an extended effect, characterized by having the following formula:

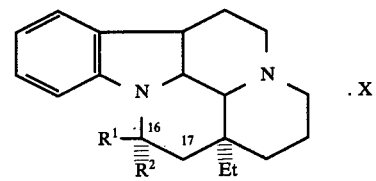

wherein, if $R_1$ is OH, $R_2$ is MeOOC, or, if $R_1$ is MeOOC, a double bond is present in the position $\Delta^{16,17}$, and X represents a group selected from the class comprising glucose-1-phosphate (neutral and acid salt), glucose-1-phosphate disodium, glucose-6-phosphate (neutral and acid salt and disodium adduct), 2,6-, 2,5-, 2,4-, 3,5-dihydroxybenzoic, p-toluensulfonic, clofibric, pivalic, 4-acetamido-butyric, 2-furoic, camphor-sulfonic, L(+)-O,O-dibenzoyltartaric, nicotinic, acetylsalicyclic, methylsulfuric, enanthic, p-chloro-phenoxyacetic, theophylline-7-acetic, caproic, capric, alginic, tannic, (D,L)-mandelic, indolyl-3-acetic, salicylic acid, hydroquinone, dihydroxyphenyl-alanine and pectin.

2. Derivative according to claim 1, characterized in that it is the adduct vincamine glucose-1-phosphate disodium or vincamine glucose-6-phosphate disodium.

3. Derivative according to claim 1, characterized in that it is vincamine glucose-1-phosphate or vincamine glucose-6-phosphate, neutral salt.

4. Derivative according to claim 1, characterized in that it is vincamine glucose-1-phosphate or vincamine glucose-6-phosphate, acid salt.

5. Derivative according to claim 1, characterized in that it is vincamine 2,4-dihydroxybenzoate.

6. Derivative according to claim 1, characterized in that it is the adduct apovincamine glucose-1-phosphate disodium or apovincamine glucose-6-phosphate disodium.

7. Derivative according to claim 1, characterized in that it is apovincamine glucose-1-phosphate or apovincamine glucose-6-phosphate, neutral salt.

8. Derivative according to claim 1, characterized in that it is apovincamine glucose-1-phosphate or apovincamine glucose-6-phosphate, acid salt.

9. Derivative according to claim 1, characterized in that it is apovincamine 2,4-dihydroxybenzoate.

10. Derivative according to claim 1, characterized in that it is vincamine or apovincamine 2,6-dihydroxybenzoate.

11. Derivative according to claim 1, characterized in that it is vincamine or apovincamine 2,5-dihydroxybenzoate.

12. Derivative according to claim 1, characterized in that it is vincamine or apovincamine 3,5-dihydroxybenzoate.

13. Derivative according to claim 1, characterized in that it is vincamine or apovincamine p-toluensulfonate.

14. Derivative according to claim 1, characterized in that it is vincamine or apovincamine clofibrate.

15. Derivative according to claim 1, characterized in that it is vincamine or apovincamine pivalate.

16. Derivative according to claim 1, characterized in that it is vincamine or apovincamine 4-acetamido-butyrate.

17. Derivative according to claim 1, characterized in that it is vincamine or apovincamine furoate.

18. Derivative according to claim 1, characterized in that it is vincamine or apovincamine D(+)-camphorsulfonate.

19. Derivative according to claim 1, characterized in that it is vincamine or apovincamine L(+)-O,O-dibenzoyltartrate.

20. Derivative according to claim 1, characterized in that it is vincamine or apovincamine nicotinate.

21. Derivative according to claim 1, characterized in that it is vincamine or apovincamine acetylsalicylate.

22. Derivative according to claim 1, characterized in that it is vincamine or apovincamine methylsulfate.

23. Derivative according to claim 1, characterized in that it is vincamine or apovincamine enanthate.

24. Derivative according to claim 1, characterized in that it is vincamine or apovincamine p-chlorophenoxyacetate.

25. Derivative according to claim 1, characterized in that it is vincamine or apovincamine theophylline-7-acetate.

26. Derivative according to claim 1, characterized in that it is vincamine or apovincamine caproate.

27. Derivative according to claim 1, characterized in that it is vincamine or apovincamine caprate.

28. Derivative according to claim 1, characterized in that it is vincamine or apovincamine alginate.

29. Derivative according to claim 1, characterized in that it is vincamine or apovincamine tannate.

30. Derivative according to claim 1, characterized in that it is vincamine or apovincamine (D, L)-mandelate.

31. Derivative according to claim 1, characterized in that it is vincamine or apovincamine indolyl-3-acetate.

32. Derivative according to claim 1, characterized in that it is vincamine or apovincamine hydroquinone adduct.

33. Derivative according to claim 1, characterized in that it is vincamine or apovincamine salicylate.

34. Derivative according to claim 1, characterized in that it is vincamine or apovincamine dihydroxyphenylalanine adduct.

35. Derivative according to claim 1, characterized in that it is vincamine or apovincamine pectin adduct in the ratio 1:1 or 2:1.

36. Pharmaceutical composition for treating cerebral arteriosclerosis having an extended effect in time and containing 40–120 mg per unit-dose of a vincamine derivative according to claim 1 with a nontoxic pharmaceutically acceptable carrier.

37. Pharmaceutical composition for treating cerebral arteriosclerosis having an extended effect in time and containing 40–160 mg per unit-dose of an apovincamine derivative according to claim 1 with a non-toxic pharmaceutically acceptable carrier.

* * * * *